United States Patent [19]

Lally

[11] Patent Number: 4,799,375
[45] Date of Patent: Jan. 24, 1989

[54] INSTRUMENTED TEST HAMMER

[75] Inventor: Richard W. Lally, Clarence, N.Y.

[73] Assignee: PCB Piezotronics, Inc., Depew, N.Y.

[21] Appl. No.: 545,625

[22] Filed: Oct. 26, 1983

[51] Int. Cl.$^4$ ............................................. G01M 7/00
[52] U.S. Cl. ..................................... 73/12; 73/DIG. 4
[58] Field of Search ............... 73/12, 82, DIG. 4, 662, 73/11; 310/328; 145/29 B

[56] References Cited

U.S. PATENT DOCUMENTS

| | | | |
|---|---|---|---|
| 2,702,060 | 2/1955 | Bonnesen | 145/29 B |
| 4,132,024 | 1/1979 | Pachmayr et al. | 42/71 P |
| 4,163,554 | 8/1979 | Bernhardt | 273/80 C |

FOREIGN PATENT DOCUMENTS

| | | | |
|---|---|---|---|
| 0082028 | 6/1980 | Japan | 73/12 |
| 0939988 | 6/1982 | U.S.S.R. | 73/12 |

Primary Examiner—David L. Lacey
Assistant Examiner—Andrew J. Anderson
Attorney, Agent, or Firm—Sommer & Sommer

[57] ABSTRACT

An instrumented test hammer for use in vibrationally exciting a test object includes a head assembly having an impact tip and a transducer operatively arranged to sense the force of an impact between the tip and object and to convert such sensed force into a proportional electrical signal, a handle extending away from the head assembly, and a cushioned grip surrounding a portion of the handle at a location spaced from the head assembly. The hammer is "tuned", by proper selection of the grip material and by selection of the ratio of the total mass of the head assembly to the combined mass of the handle and grip, such that the node of the first translational resonant mode of the hammer, after impacting against an object, is located substantially proximate the head assembly, independently of the manner by which the grip is held. The improved hammer substantially avoids the generation of spurious electrical signals due to post-impact vibration of the head assembly.

19 Claims, 4 Drawing Sheets

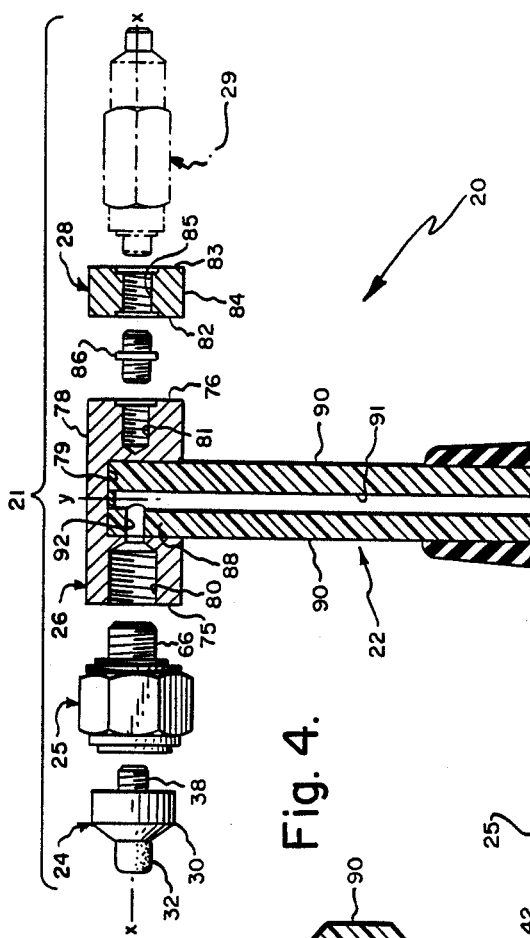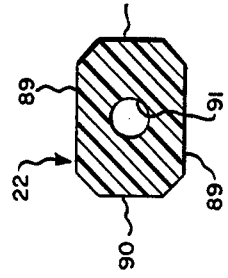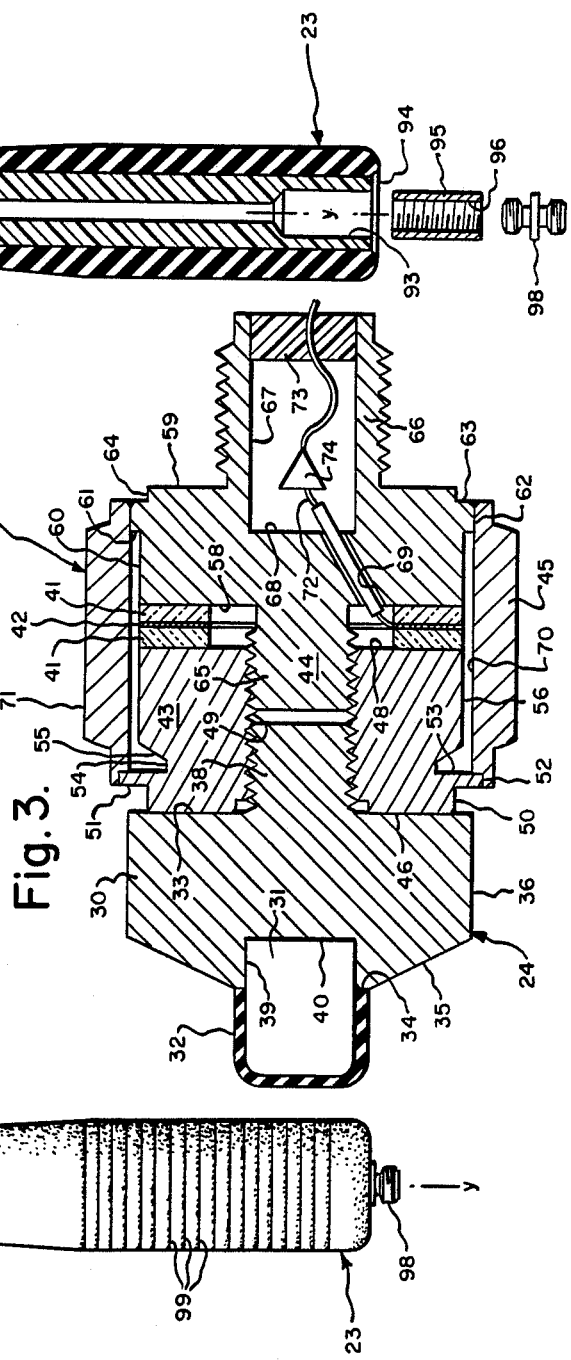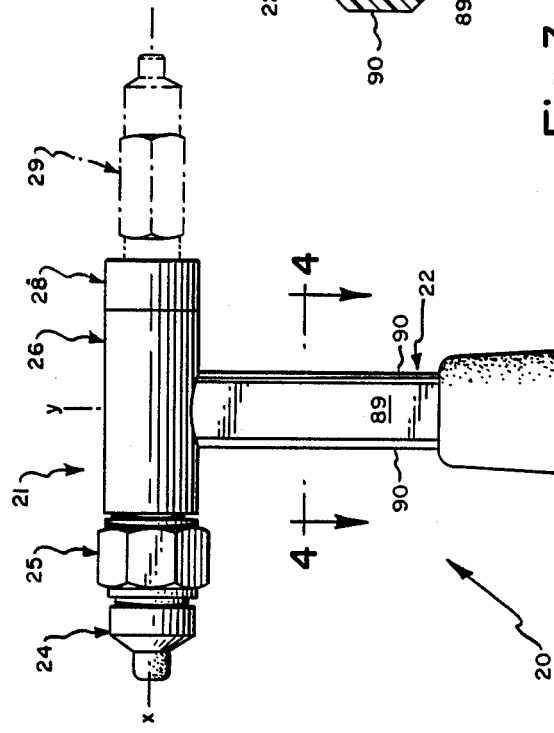

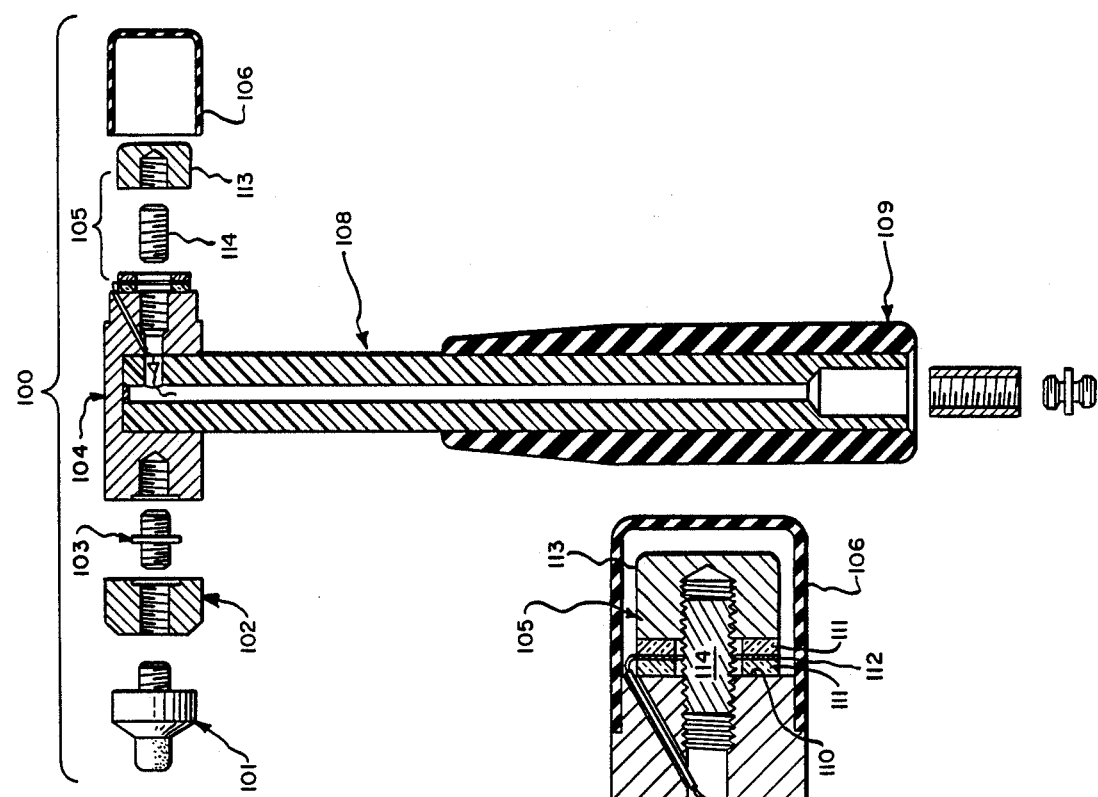
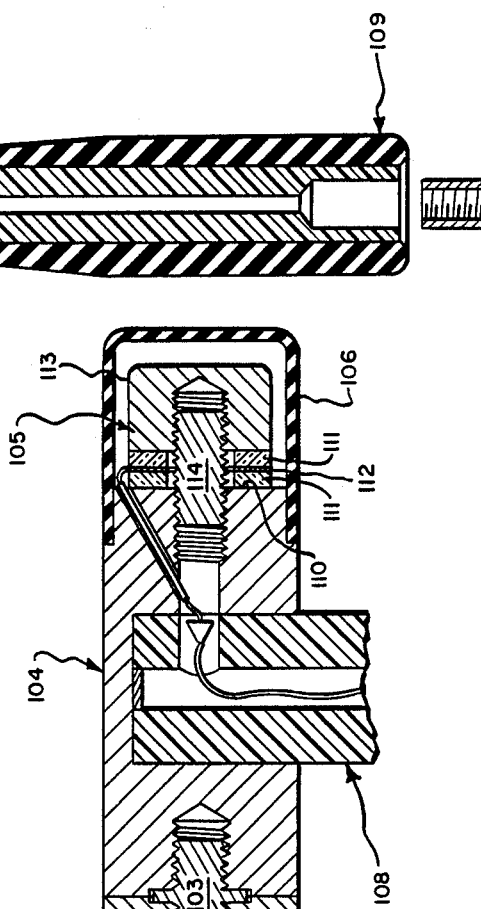
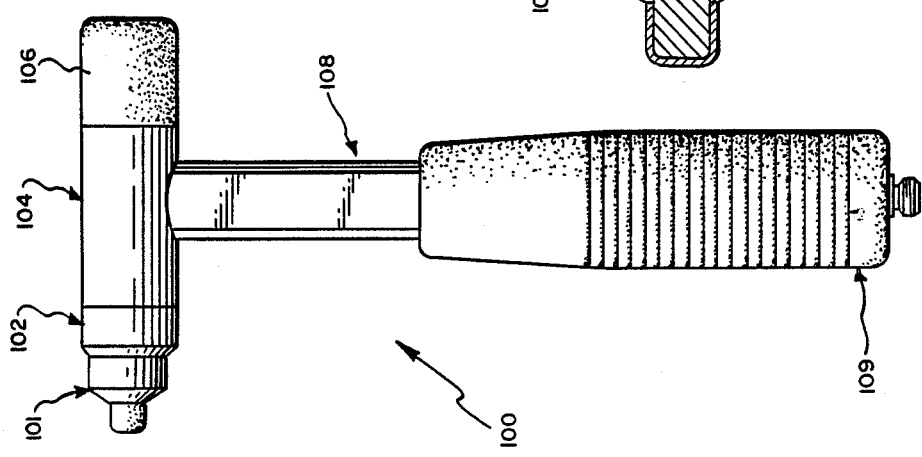
Fig. 6.
Fig. 7.
Fig. 5.

Fig. II.
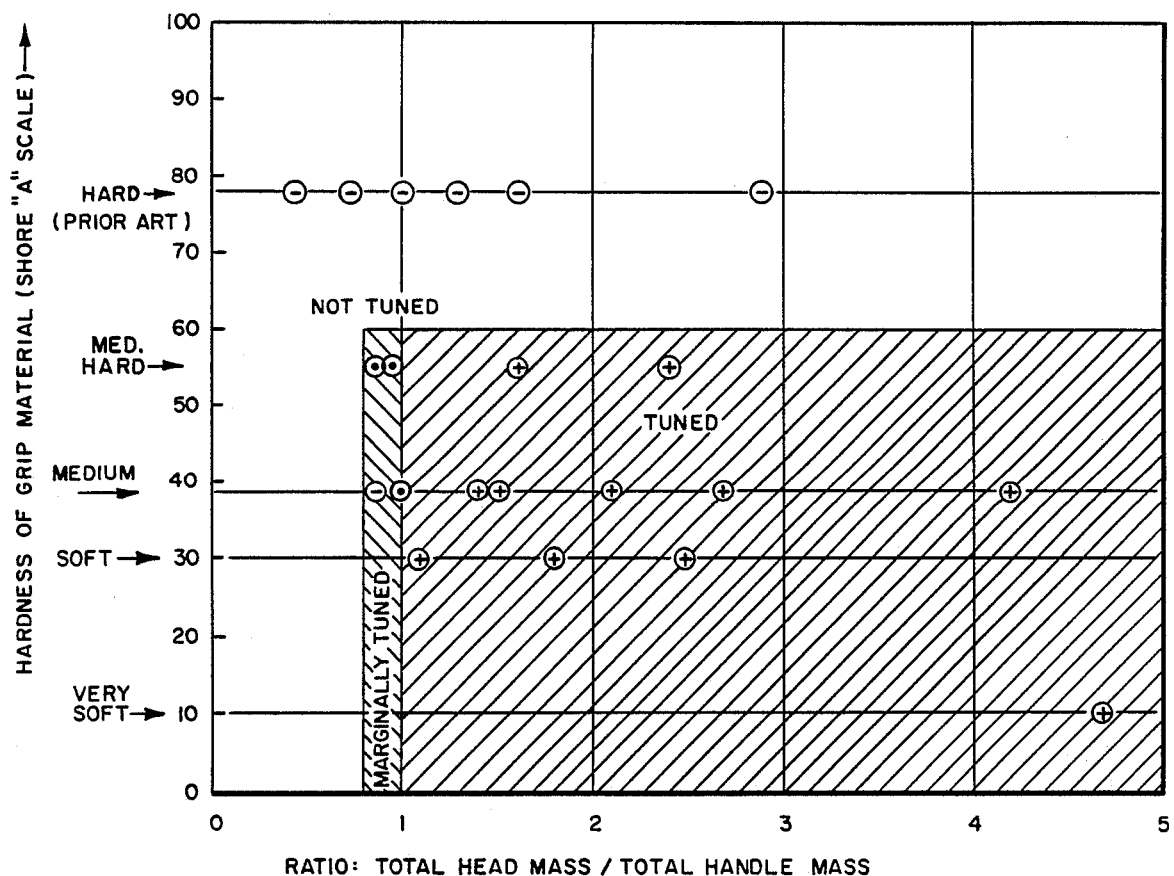

INSTRUMENTED TEST HAMMER

BACKGROUND OF THE INVENTION

1. Field of the Invention

The present invention relates generally to the field of instrumented test hammers, and, more particularly, to an improved test hammer which avoids spurious electrical signals and glitches due to post-impact vibration of the head assembly.

2. Description of the Prior Art

Instrumented test hammers for exciting a test object have been developed heretofore. Such prior art test hammers have included a head assembly, a handle extending away therefrom, and a graspable grip mounted on the distal end of the handle. The head assembly included an impact tip, and one or more piezo-electric crystals held under a preload between the tip and another mass. Thus, when the hammer was caused to impact against an object, the piezo-electric crystals would produce an analogous electrical signal proportional to the force of the impact. Prior art grips were of a relatively-hard resilient material having a hardness of about 78 on a Shore "A" scale when measured with a durometer.

Details of such earlier hammers, and their uses and applications, are representatively shown and described in one or more of the following prior art references: Halverson and Brown "Impulse technique for structural frequency result testing", Sound and Vibration, November 1977 (pp 8–21); Lally, "Testing the Behavior of Structures", Test, August/September 1978; R. W. Lally, "Transduction", PCB Piezotronics, Inc. (1981); "Stress Waves in a Long Bar", PCB Piezotronics, Inc. (1974); "Piezo-electric Analogies", Electromechanical Design, December 1967 (pp. 52-53).

However, upon information and belief, such prior art instrumented test hammers were somewhat limited in their application and use because the data produced thereby depended largely upon the expertise of the particular operator, which varied from individual to individual. The operator's hand and arm often became, in effect, part of the hammer structure, and introduced additional mass, stiffness and damping. At times, this enhanced post-impact vibration of the head assembly, and frequently caused spurious oscillation of the generated electrical signal, which destroyed the proportionality of the signal to the force of impact. Sometimes, the dynamic behavior of such hammers caused an undesirable "double hit" against the object, with the production of a corresponding oscillation in the spectrum of the electrical signal. Also, resonances of the hammer structure appearing in the test results were often mistaken for dynamic behavior of the object being tested.

SUMMARY OF THE INVENTION

The present invention provides an improved instrumented test hammer for use in exciting a test object, which hammer is independently "tuned" such that the electrical signal produced thereby will be substantially proportional to the force of an impact, independent of the skill or expertise of a particular operator.

The improved test hammer broadly includes a head assembly having an impact tip and having a transducer operatively arranged to sense the force of an impact between the object and tip and to convert such sensed force into a proportional electrical signal; a handle connected to the head assembly and extending away therefrom; and a cushioned grip surrounding a portion of the handle at a location spaced from the head assembly. The grip is selected of a material having a hardess of not more than 60 on a Shore "A" scale. The handle and head assembly are so dimensioned and proportioned, by adjusting the ratio of the total mas of the head assembly to the combined mass of the handle and grip, that the node of the first translational mode of the hammer, in the plane of the direction of impact and the axis of the handle, after impacting against an object, will be located substantially proximate the head assembly, independently of the manner by which the grip is held, thereby to substantially avoid the generation of spurious electrical signals due to post-impact vibration of the head assembly.

Accordingly, the general object of the present invention is to provide an improved instrumented test hammer for vibrationally exciting an object.

Another object is to provide an improved test hammer which minimizes post-impact vibration of the head assembly.

Another object is to provide an improved test hammer, the use of which does not depend upon the expertise of a particular operator.

Another object is to provide an improved test hammer which is capable of auto-calibration.

These and other objects and advantages will become apparent from the foregoing ad ongoing written specification, the drawings, and the appended claims.

BRIEF DESCRIPTION OF THE DRAWINGS

FIG. 1 is a side elevation of an improved test hammer employing a force transducer, this view also illustrating an optional accelerometer (shown in phantom) as being mounted on the head assembly for use in calibrating the signal generated by the transducer.

FIG. 2 is a fragmentary exploded view thereof, this view showing the handle, grip, and portions of the head assembly in vertical section, but still showing the impact tip, the transducer, and the accelerometer in elevation.

FIG. 3 is an enlarged fragmentary vertical sectional view of the impact tip and the force transducer shown in FIGS. 1 and 2.

FIG. 4 is a fragmentary horizontal sectional view of the handle, this view being taken generally of line 4—4 of FIG. 1.

FIG. 5 is a side elevation of another form of the improved test hammer, this embodiment employing an accelerometer as the force sensing element.

FIG. 6 is a vertical section view thereof, this view illustrating the various component parts in exploded aligned relation to one another, but still depicting the impact tip in elevation.

FIG. 7 is an enlarged fragmentary vertical sectional view of the head assembly.

FIG. 11 is a chart of hardness of grip material versus ratio of total head mass to combined mass to handle and grip, this view illustrating at various points, particular combinations of different grip materials and different ratios, and whether the resultant hammer was non-tuned marginally-tuned, or completely-tuned so as to be independent of the manner by which the grip was held.

DESCRIPTION OF THE PREFERRED EMBODIMENTS

Figure 8:
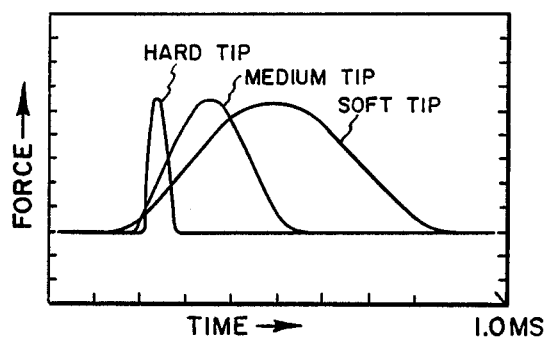
FIG. 8 is a graph of impact force versus time for three different tips.

At the outset, it should be clearly understood that like reference numerals are intended to identify the same structural elements, portions or surfaces consistently throughout the several drawing figures, as such elements, portions or surfaces may be further described or explained by the entire written specification of which this detailed description is an integral part. Unless otherwise indicated, the drawings are intended to be read (e.g., cross-hatching, data, charts, graphs, dimensions, proportions, etc.) together with the specification, and are to be construed as a portion of the entire "written description" of this invention, as required by 35 U.S.C. §112. As used in the following description, the terms "leftwardly" and "rightwardly" refer to the orientation of the illustrated structure as a particular drawing figure faces the reader, and terms "inwardly" and "outwardly" refer to the orientation of a surface relative to its axis.

FORCE TRANSDUCER EMBODIMENT (FIG. 1-4)

Referring now to the drawings, and, more particularly, to FIGS. 1-4 thereof, this invention provides an improved instrumented test hammer, of which a first preferred embodiment is generally indicated at 20, for use in vibrationally exciting a test object (not shown). Test hammer 20 is shown as broadly including an uppermost head assembly 21, a vertically-elongated handle 22 depending from the head assembly, and a cushioned grip 23 mounted the lower marginal end portion of the handle.

The head assembly is shown as being horizontally elongated along axis x—x, and is typically of sectional construction. Specifically, the head assembly includes (from left to right in FIGS. 1 and 2) an impact tip 24, a force transducer 25, a body 26, and a tuning mass 28. An optional accelerometer, shown in phantom and generally indicated at 29, is mounted axially on the tuning mass and extends rightwardly therefrom. Accelerometer 29 is used for calibrating the electrical signal produced by the force transducer. Hence, while depicted in the drawings for use in describing the calibration feature, infra, the presence of the accelerometer is otherwise collateral to the structure and operation of hammer assembly 20. In other words, after the force transducer has been calibrated, accelerometer 29 may be entirely removed.

Referring now to FIGS. 2 and 3, impact tip 24 is shown as including a specially-configured solid metal body 30, an insert 31, and a vinyl cap 32. The body has an annular vertical right face 33; a left face including a leftwardly-facing annular vertical surface 34 and a leftwardly- and outwardly-inclined frusto-conical surface 35, and an outwardly-facing cylindrical outer surface 36 joining the marginal ends of surfaces 34,35. As best shown in FIG. 3, an integrally-formed externally-threaded stem 38 extends rightwardly from right face 33. A recess extends axially into the tip body from its left face surface 34. This recess is bounded by an inwardly-facing cylindrical surface 39 extending rightwardly from surface 34, and a leftwardly-facing circular vertical bottom surface 40. The tip insert 31 is shown as being horizontally-elongated substantially-cylindrical solid member. The right marginal end portion of the insert is received in the body recess. The remainder of the insert extends leftwardly of tip surface 34. Normally, the insert is held in the recess of the tip body by means of a press-fit or a suitable adhesive. Depending upon the frequency range of interest, the tip inserts may be typically formed of rubber (soft), plastic (intermediate), or steel (hard). The cap 32 is a somewhat cup-shaped member protectively covering the leftward exposed portion of the insert. Thus, the operator may readily mount an impact tip 24, having an insert of desired hardness, on the force transducer 25. If the contact between the tip and test object is axial, then the full impact force exerted by the object on the tip will be transmitted to the force transducer.

Referring to FIG. 3, the force transducer 25 is shown as including a three-part sectional body, and a pair of annular disc-like piezo-electric plates 41,41, preferably quartz crystals, with an electrode 42 sandwiched therebetween. The transducer body includes a left part 43, a right part 44, and an outer part 45. The left part is a specially-configured member having annular vertical left and right faces 46,48, respectively; an internally-threaded through-bore 49; and an outer surface which includes (from left to right in FIG. 3) an outwardly-facing cylindrical surface 50 extending rightwardly from left face 46, a leftwardly-facing annular vertical surface 51, an outwardly-facing cylindrical surface 52, a rightwardly-facing annular vertical surface 53, an outwardly-facing cylindrical surface 54, a leftwardly- and outwardly-facing frusto-conical surface 55, and an outwardly-facing cylindrical surface 56 continuing rightwardly therefrom to join right face 48. The stem 38 of impact tip 24 is matingly received in the left marginal end portion of left part bore 49, such that impact tip surface 33 abuts left part face 46.

The body right part 44 is another specially-configured member, and is bounded by annular vertical left and right faces 58,59, and an outer surface including (from left to right in FIG. 3) an outwardly-facing cylindrical surface 60 extending rightwardly from left face 58, a leftwardly-facing annular vertical surface 61, an outwardly-facing cylindrical surface 62, a rightwardly-facing annular vertical surface 63, and an outwardly-facing cylindrical surface 64 continuing rightwardly therefrom to join right face 59. Integrally-formed externally-threaded stems 65,66 extend leftwardly and rightwardly from right part faces 58,59, respectively. Left stem 65 is matingly received in the right marginal end portion of left part bore 49. A recess extends leftwardly into the body right part from the distal end of stem 66. Specifically, this recess is bounded by an inwardly-facing cylindrical surface 67 and a rightwardly-facing circular vertical bottom surface 68. A passageway 69 communicates bottom surface 68 with left face 58 to accommodate passage of a wire from electrode 42. Thus, the right part of the transducer body is threaded into the left part thereof such that the crystal-electrode-crystal subassembly is compressively sandwiched, or preloaded, between body surfaces 48,58 to the extent desired.

The body outer part 45 is a tube-like member connecting the body left and right parts. Outer part 45 is shown as having an inwardly-facing cylindrical inner surface 70, the right marginal end portion of which engages surface 62. The left marginal end portion of the outer part is provided with an annular corner notch in which the edge between left part surfaces 52,53 is received. The outer part is provided with an external hexagonal surface 71, to facilitate grasping and rotation by a suitable turning tool (not shown). When the piezoelectric crystals have been preloaded (i.e., axially compressed between body surfacs 48,58) to the extent desired, outer part 45 is suitably welded to the body left and right parts, as shown, to prevent unintended separation of the transducer assembly. An insulated conductor 72 is connected to electrode 42, passes through passageway 69, the right stem recess, and an epoxy plug 73 sealing the open mouth of the recess. A MOSFET isolation amplifies 74, inter alia, is connected in series with conductor 72 to make the signal from the crystals compatible with commercial signal processing or displaying instruments.

Referring now to FIG. 2, the head assembly body 26 is show as being a solid member having annular vertical left and right faces 75,76, respectively, and an outwardly-facing cylindrical surface 78 extending therebetween. A blind recess 79, having a cross-sectional shape complementarily-configured to that of the handle, extends radially upwardly into the body from its underside. A tapped recess 80 extends rightwardly into body 26 from its left face 75 and communicates with recess 79. Recess 80 is adapted to receive threaded insertion of transducer stem 66 such that transducer right face 59 will abut body left face 75. A blind tapped recess 81 extends leftwardly into body 26 from its right face 76.

The tuning mass 28 is a weight of such density, dimension and proportion that the portion of the head assembly mass which is to the left of handle axis y—y substantially equals and balances the portion of the head assembly mass which is to the right of the handle axis. This latter portion, of course, excludes the mass of accelerometer 29, which is only used to calibrate the signals generated by crystals 41,41 and is thereafter removable from the head assembly. The tuning mass is shown as being a disc-like element having annular vertical left and right faces 82,83, respectively, a cylindrical outer surface 84, and a tapped through-hole 85. The tuning mass is mounted on the head assembly body 26 by means of a mounting stud 86 such that the left face 82 of the tuning mass abuts the body right face 76.

The handle 22 is a tubular member, and is shown as being vertically elongated along axis y—y. An upper marginal end portion 88 of the handle is received in body recess 79, while balance of the handle extends away from the head assembly body 26. Handle axis y—y is shown as being vertical, and, therefore, perpendicular or normal to head assembly axis x—x, but this is not cricical or invariable and the angle between these two axes may be varied. As best shown in FIG. 4, the handle has a substantially rectangular cross-section, with chamfered corners. The longer sides 89,89 of the handle are arranged in planes which intersect axis x—x. As best shown in FIG. 2, handle 22 is provided with an axial vertical through-hole 91. A horizontal hole 92 is drilled into the handle upper marginal end portion from the forward surface 90 thereof to intersect vertical hole 91. When the hammer is assembled, hole 92 communicates with body recess 80 so that the condcutor 72 issuing from the force transducer may pass through holes 80,92, and 91, and therefore be concealed with the hollow handle. An axial recess 93 extends upwardly into the handle from its lower distal end face 94, so as to receive insertion a tubular sleeve 95 having a tapped through-bore 96. An electrical connector 98, which somewhat resembles a mounting stud in outward appearance, is threaded upwardly into the lower marginal end portion of sleeve bore 96, and is suitably connected to conductors 72. Thus, a suitable connecting cable (not shown) may be readily and releasably coupled to the hammer to convey the signals in conductors 72 to other structure (not shown). In some cases, handle 22 may be formed of a relatively light-weight material, such as balsa wood (having a density of about 7.5–12.5 lbs/ft$^3$) or a graphite fiber epoxy material (having a density of about 80–100 lbs/ft$^3$). These examples are illustrative only, for it is the ratio of the total mass of the head assembly relative to the combined mass of the handle and grip that is deemed to be important, as discussed infra.

Grip 23 is shown as surrounding a lower marginal end portion of the handle at a location spaced from the head assembly. The outer surface of the grip is shown as being provided with a plurality of ribs, severally indicated at 99, to facilitate grasping by the hand of an operator. The grip is formed of a resilient cushioned material, such as neoprene rubber, having a hardness of not more than 60 on a Shore "A" scale. The grip may be formed of a material which is "very soft" (i.e., having a hardness of within 5–15, and preferably about 10, on a Shore "A" scale), "soft" (i.e., having a hardness of 25–34, and preferably about 30, on a Shore "A" scale), "medium" (i.e., having a hardness of 34–44, and preferably about 39, on a Shore "A" scale), or "medium hard" (i.e., having a hardness of 50–60, and preferably about 55, on a Shore "A" scale).

Hammer 20 is assembled as shown in FIG. 1. The operator may grasp the cushioned grip and tap the impact 24 against an object-to-be-tested. The impact of the hammer against the object will exert a force on the tip, which force will be transmitted to the crystals. Such further compression will cause the piezo-electric crystals to generate an analogous electrical signal which will be proportional to the force of the impact. This signal may be tapped off at cable connector 98.

In order to calibrate the signals, an accelerometer is temporarily mounted on the tuning mass, and the tip of the hammer is again caused to impact against an object. The accelerometer has another pair of piezo-electric crystals compressed under preload between a body and a siesmic mass. Since the accelerometer is mounted on the head assembly, it is subjected to the acceleration caused by the same impact force that the force transducer experiences. The accelerometer has a known sensitivity, may be used to determine the magnitude of the impact force. Once this is known, the sensitivity of the force transducer may be readily calibrated. Thereafter, the accelerometer may be removed from the improved hammer until calibration is desired. This auto-calibration technique is made possible by "tuning" the hammer structure, which effectively isolates the head assembly from the handle and grip, as well as the operator's hand.

ACCELEROMETER EMBODIMENT (FIGS. 5–7)

A second embodiment of the improved test hammer is generally indicated at 100 in FIGS. 5–7. Whereas the first embodiment employed a force transducer (e.g., 25) to convert the force of an impact into a proportional electrical signal, this second embodiment employs an accelerometer as the sensing and converting element. Since much of the structure of this second embodiment corresponds to structure previously described, the ensuing description will be somewhat abbreviated.

Referring now to FIGS. 5–7, test hammer 100 is shown as including a head assembly having (from left to right) an impact tip 101, a tuning mass 102, a mounting stud 103 for connecting the mass to a body 104, and an accelerometer, generally indicated at 105, and protectively enclosed with a cup-shaped cover 106; a handle 108 extending away from the head assembly, and a cushioned grip 109 surrounding the lower marginal end portion of the handle at a location spaced from the head assembly.

As best shown in FIG. 7, the head assembly body 104 has an annular vertical right face 110, which functions as the base of the accelerometer. The accelerometer includes two piezo-electric crystals 111,111, again preferably quartz, with a metallic electrode 112 sandwiched therebetween. Each of the crystals is an annular disc-like element. The crystal-electrode-crystal subassembly is compressed between surface 110 and the facing surface of a seismic mass 113, by means of a preload stud 114 engaging the base and mass. Thus, when the tip of the hammer is caused to impact against an object, the crystals will be further compressed, and will thereby generate an electrical signal proportional to the sensed acceleration. According to Newton's second law, force is equal to the product of mass and acceleration (i.e., $F=ma$). Hence, acceleration is proportional to force, for a constant mass. Thus, the product of this sensed acceleration and the head assembly mass will be the force of the impact. Of course, the signal may be calibrated so as to indicate force directly.

OPERATION

As previously noted, the impact tips are interchangeable, depending upon the particular application. An appropriate impact tip, having an insert of desired hardness, may be selected depending upon the frequency range of interest. FIG. 8 is a graph of force (ordinate) versus time (abscissa) for impact tips having hard (i.e., steel), medium (i.e., plastic), and soft (i.e., rubber) inserts. Thus, an insert with a hard tip will produce the shortest pulse width time-history waveform, while the insert with a soft tip will produce the longest waveform.

Figure 9:
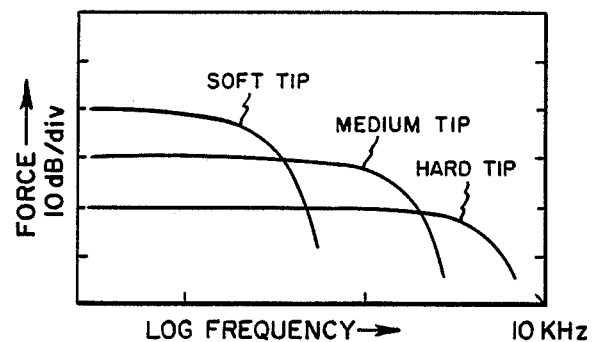
FIG. 9 is a graph of impact force versus frequency for the three tips depicted in FIG. 8.

As shown in FIG. 9, when such force signal is processed and displayed against frequency, it is seen that the impact will excite the object with substantially constant force over a frequency range. FIG. 9 also illustrates that frequency range is greatest for the hard insert, and least for the soft insert. Of course, the frequency range of the medium insert is intermediate these two extremes.

Figure 10:
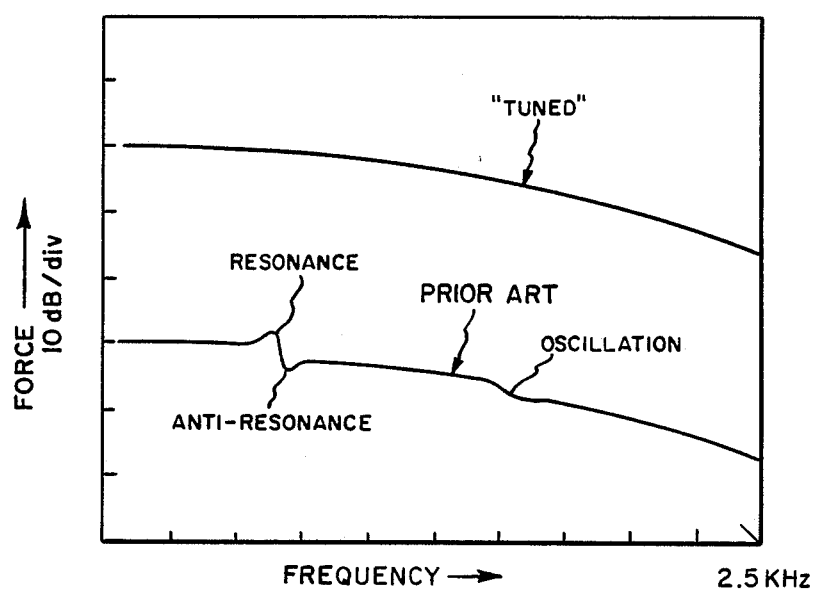
FIG. 10 is an enlarged graph of impact force versus frequency of a portion of the graph shown in FIG. 9, this graph comparing the performance of a "tuned" hammer and a prior art hammer.

FIG. 10 is an enlargement of a portion of the force (ordinate) versus frequency (abscissa) curve for the hard tip shown in FIG. 9. In FIG. 10, the performance of an improved "tuned" hammer according to the present invention is displayed above that of an "untuned" prior art hammer. Persons skilled in this art will appreciate that the illustrated portions of these performance curves are displayed above and below one another for clarity of illustration, and not as direct measurements of the indicated force. In other words, the corresponding portion of the curve of the prior art hammer may be viewed as having been shifted downwardly only so that it may be separated from and visually compared with the performance of the improved "tuned" hammer. The significance of FIG. 10 is that, whereas the curve of the prior art hammer had various resonant peaks and other anomalies, the curve of the improved hammer is peak-free and is smooth and continuous. Such spurious anomalies and peaks of the prior art hammer are thought to be caused by post-impact vibration of the head assembly at its natural resonant frequencies. Since force and acceleration are directly related (i.e., $F=ma$), post-impact vibration of the prior art head assembly produced various accelerations on the sensing and converting element, which, in turn, produced spurious force signals.

THE IMPROVED "TUNED" HAMMER

Upon information and belief, source of resonant peaks, anti-resonant valleys, and anomalies in prior art hammers was such post-impact vibration of the head assembly. However, the magnitude of such spurious signals seemed to vary from operator to operator. In hindsight, it is now thought that this difference in result depended, at least in part, on the strength of the operator's grasp on the grip of the handle. One operator might grasp the grip too tightly, and such rigidization effectively caused his hand, and possibly his arm, to become, in effect, an extension of the handle itself. Another operator might grasp the grip loosely, thereby permitting additional freedom for the handle to vibrate after impact. The point of this is that the accuracy of such prior art hammers depended largely upon the expertise of a particular operator.

The aim of the present improvement is to "tune" the structure of the test hammer such that the node of at least the first translational resonant mode of the hammer, in the plane of the direction of impact and the handle axis (i.e., in a plane including axes (x—x and y—y), after impacting against the object, will be located substantially proximate the head assembly in a manner substantially independent of the manner by which the grip is held. It may be desirable to have a node of the second resonant mode also located proximate the head assembly. With this or these nodes located proximate the head, the head assembly will not vibrate substantially at this or these resonant frequencies, and, consequently, spurious signals due to post-impact vibration of the head assembly will not be generated. Thus, "tuning" essentially involves changing the geometry of the mode shape so as to reduce post-impact vibration of the head assembly. Thus, the generated electrical signal will not depend upon the strength of the operator's grasp. At the same time, it is desired to have a wide range of hammer sizes. Small tap hammers are used to test small delicate parts, while large sledge hammers are used to test large structures, such as bridges and the like. Based on emperical data, the improved hammers are "tuned" by varying the ratio of the total head mass to the combined mass of the handle and grip, and by using an improved grip material which allows the handle additional freedom to vibrate after impact and provides some damping. The aforementioned emperical data is illustrated in FIG. 11.

A line of prior art test hammers made by applicant's assignee, PCB Piezotronics, Inc. of Depew, N.Y., had a variety of relative mass ratios. However, the grip material was hard, having a hardness of about 79 on a Shore "A" scale. None of these prior art test hammers was "tuned" so as to be completely independent of the manner by which the grip was held.

Applicant has discovered that an instrumented test hammer, such as previously indicated at 20 and 100, may be "tuned" so as to be substantially independent of the expertise of a particular operator. As is now understood, a hammer may be "tuned" by varying the hardness or softness of the grip material, and by altering the structure of the hammer such that the ratio of the total mass of the head assembly to the combined mass of the handle and grip, is at least 1.0. The mass of a particular handle is a function of the density of the material of which the handle is made, as well as its cross-sectional shape and length. The realization of these critical limitations (i.e., grip material and mass ratio) has enabled the manufacture of a variety of test hammers, all consistently "tuned", albeit of different physical dimensions and proportions. The mass of the head assembly may be modified by addition of one or more "tuning" masses, of suitable dimensions and weight. For a small hammer, a light-weight handle, such as formed of balsa wood or graphite fiber/epoxy, may be employed. It has been applicant's experimental experience, as shown in FIG. 11, that if the grip is formed of a hard material (i.e., having a hardness of more than about 60 on a Shore "A" scale), as in the prior art hammers, regardless of the relative mass ratio, the hammer will not be predictably "tuned" so as to be substantially independent of the strength of the operator's grip and his particular expertise. On the other hand, even if a softer grip material is used, the hammer will not be independently "tuned" if the relative mass ratio is less than about 1.0. However, for softer grip materials and ratios greater than 1.0, applicant's emperical data and manfuacturing experience suggest that the hammer will be predictably "tuned". At the present time, applicant is unaware of an upper limit to this relative mass ratio. Thus, whether the hammer is "tuned" or not appears to depend upon both variables, possibly inter alia.

The present invention contemplates that many changes may be made. For example, the various component parts may be of sectional construction, or may be formed integrally, as desired. The various materials of construction may be varied with predictable result. For balance, proper dimensions are a function of the density of the particular material selected. Many different materials are suitable for use as the handle, consistent with the overall design criteria. While quartz is a preferred piezo-electric material, other piezo-electric materials may be substituted therefor. Indeed, the transducer need not necessarily employ a piezo-electric material as the sensing and converting mechanism. Additional mass may be readily added to the head assembly, and/or additional damping may be added to the handle or grip, as desired. Therefore, while the two presently-preferred embodiments of the improved test hammer have been shown and described, and several modifications thereof discussed, persons skilled in this art will readily appreciate that various additional changes and modifications may be made without departing from the spirit of the invention, as defined and differentiated by the following claims.

What is claimed is:

1. An instrumented test hammer for use in exciting a test object, comprising:
   a head assembly having an impact tip and having a transducer operatively arranged to sense the force of an impact between said tip and object and to covert such force into a proportional electrical signal;
   an elongated handle connected to said head assembly and extending away therefrom;
   a cushioned grip surrounding a portion of said handle at a location spaced from said head assembly;
   said grip being formed of a suitable material and said head assembly, handle and grip being so dimensioned and proportioned such that the node of the first translational resonant mode of said hammer, in the plane of the direction of impact and the handle axis, after impacting against said object, is located substantially proximate said head assembly and substantially independently of the manner by which said grip is held;
   thereby to substantially avoid the generation of spurious electrical signals due to post-impact vibration of said head assembly.

2. An instrumented test hammer as set forth in claim 1 wherein said handle is formed of a material having a density of about 7.5–12.5 lbs/ft$^3$.

3. An instrumented test hammer as set forth in claim 2 wherein said handle is formed of balsa wood.

4. An instrumented test hammer as set forth in claim 1 wherein said handle is formed of a graphite fiber material.

5. An instrumented test hammer as set forth in claim 4 wherein said handle is hollow.

6. An instrumeted test hammer for use in exciting a test object, comprising:
   a head assembly having an impact tip and having a transducer operatively arranged to convert the force of an impact between said object and tip into a proportional electrical signal;
   an elongated handle connected to said head assembly and extending away therefrom;
   a cushioned grip surrounding a portion of said handle at a location spaced from said head assembly, said grip having an outer surface which is adapted to be grasped by an operator, said grip being formed of a material having a hardness of not more than 60 on a Shore "A" scale;
   said handle being selected of a material and being so dimensioned and proportioned that the ratio of the total mass of said head assembly to the combined mass of said handle and grip is at least 1.0, such that the node of the first translational resonant mode of said hammer, in the plane of the direction of impact and the handle axis, after impacting against said object, is located substantially proximate said head assembly and substantially independently of the manner by which said grip is held; thereby to substantially avoid the generation of spurious electrical signals due to post-impact vibration of said head assembly.

7. An instrumented test hammer as set forth in claim 6 wherein said grip is formed of a material having a hardness of 50–60 on a Shore "A" scale.

8. An instrumented test hammer as set forth in claim 7 wherein said grip is formed of a material having a hardness of about 55 on a Shore "A" scale.

9. An instrumented test hammer as set forth in claim 6 wherein said grip is formed of a material having a hardness of 34–44 on a Shore "A" scale.

10. An instrumented test hammer as set forth in claim 9 wherein said grip is formed of a material having a hardness of about 39 on a Shore "A" scale.

11. An instrumented test hammer as set forth in claim 6 wherein said grip is formed of a material having a hardness of 25–34 on a Shore "A" scale.

12. An instrumented test hammer as set forth in claim 11 wherein said grip is formed of a material having a hardness of about 30 on a Shore "A" scale.

13. An instrumented test hammer as set forth in claim 6 wherein said grip is formed of a material having a hardness of 5–15 on a Shore "A" scale.

14. An instrumented test hammer as set forth in claim 13 wherein said grip is formed of a material having a hardness of about 10 on a Shore "A" scale.

15. An instrumented test hammer as set forth in claim 6 wherein said handle is formed of a material having a density of about 7.5–12.5 lbs/ft$^3$.

16. An instrument test hammer as set forth in claim 15 wherein said handle is formed of balsa wood.

17. An instrumented test hammer as set forth in claim 6 wherein said handle is formed of a graphite fiber material.

18. An instrumented test hammer as set forth in claim 17 wherein said handle is hollow.

19. An instrumented test hammer as set forth in claim 6 wherein said handle is formed of a material having a density of about 80–100 lbs/ft$^3$.

* * * * *